(12) United States Patent
Ito

(10) Patent No.: US 7,932,014 B2
(45) Date of Patent: Apr. 26, 2011

(54) PHOTOSENSITIVE COMPOUND, PHOTOSENSITIVE COMPOSITION, RESIST PATTERN FORMING METHOD, AND DEVICE PRODUCTION PROCESS

(75) Inventor: Toshiki Ito, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/067,898

(22) PCT Filed: Feb. 14, 2008

(86) PCT No.: PCT/JP2008/053002
§ 371 (c)(1),
(2), (4) Date: Mar. 24, 2008

(87) PCT Pub. No.: WO2008/111378
PCT Pub. Date: Sep. 18, 2008

(65) Prior Publication Data
US 2010/0221656 A1 Sep. 2, 2010

(30) Foreign Application Priority Data

Feb. 20, 2007 (JP) ................. 2007-040004

(51) Int. Cl.
*G03F 7/039* (2006.01)
*G03F 7/20* (2006.01)
*G03F 7/30* (2006.01)
*G03F 7/095* (2006.01)
*C07C 69/753* (2006.01)

(52) U.S. Cl. ............ 430/270.1; 430/326; 430/311; 430/312; 430/313; 430/317; 568/719; 568/718; 568/720; 568/722; 568/723; 568/726; 568/733; 549/388; 549/390; 549/391; 560/8; 560/55; 560/56; 560/64; 560/65; 560/73

(58) Field of Classification Search ................ None
See application file for complete search history.

(56) References Cited

U.S. PATENT DOCUMENTS

| 4,859,563 | A | 8/1989 | Miura et al. |
| 5,258,265 | A | 11/1993 | Slater et al. |
| 6,849,391 | B2 | 2/2005 | Yamaguchi et al. |
| 7,022,463 | B2 | 4/2006 | Yamaguchi et al. |
| 2005/0221222 | A1 | 10/2005 | Ito et al. |
| 2006/0003269 | A1 | 1/2006 | Ito et al. |
| 2006/0014108 | A1 | 1/2006 | Ito et al. |
| 2007/0287105 | A1 | 12/2007 | Ito et al. |
| 2010/0044628 | A1* | 2/2010 | Brammer et al. ........ 252/182.12 |

FOREIGN PATENT DOCUMENTS

JP 61-153632 A 7/1986

OTHER PUBLICATIONS

Derwent English abstract of JP 61153632 (Isori).*
Tokuyuki Honda et al., "What Determines the Ultimate Resolution? The Critical Relationship Between Exposure Tools and Photoresists," Optical Microlithography XIX, edited by Donis G. Flagello, Proc. of SPIE vol. 6154, 6154221-1-615422-9 (2006) (no month).
D.H.R. Barton et al., "Photochemical Transformations. Part XIX. Some Photosensitive Protecting Groups," J. Chem. Soc. 3571-78 (May 1965).
Taku Hirayama et al., "New Photoresist Based on Amorphous Low Molecular Weight Polyphenols," 17(3) J. Photopoly. Sci. Technol. 435-40 (2004) (No Month).

* cited by examiner

*Primary Examiner* — Sin J. Lee
(74) *Attorney, Agent, or Firm* — Fitzpatrick, Cella, Harper & Scinto

(57) ABSTRACT

A photosensitive compound has two or more structural units, in a molecule, represented by the following general formula (1):

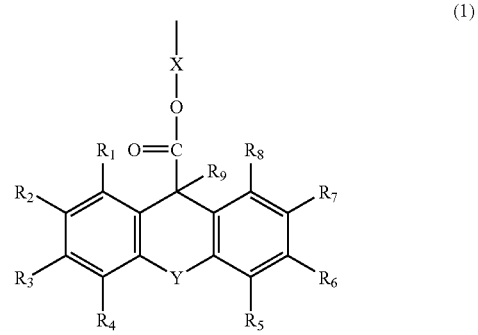

(1)

wherein $R_1$ to $R_8$ are selected from the group consisting of a hydrogen atom, a halogen atom, an alkyl group, an alkoxy group, an acetoxy group, a phenyl group, a naphthyl group, and an alkyl group in which some or all of the hydrogen atoms are optionally replaced by fluorine atoms; $R_9$ is a hydrogen atom or a hydroxyl group; X is a substituted or unsubstituted phenylene group or a substituted or unsubstituted naphthalene group; and Y is an oxygen atom or a single bond.

17 Claims, 2 Drawing Sheets

PHOTOSENSITIVE COMPOUND, PHOTOSENSITIVE COMPOSITION, RESIST PATTERN FORMING METHOD, AND DEVICE PRODUCTION PROCESS

TECHNICAL FIELD

The present invention relates to a photosensitive compound, a photosensitive composition containing the photosensitive compound dissolved in a solvent, a resist pattern forming method using the photosensitive composition, and a process for producing a device by using the resist pattern forming method.

BACKGROUND ART

In recent years, demand has continued to increase for various high-density and high-integration electronic devices that require fine processing, including a semiconductor device. In a semiconductor device production process, a photolithographic process (photolithography) plays an important role in forming a fine pattern. In the photolithography, a technique capable of stably performing fine processing with an accuracy of 100 nm or less is required. For this reason, a resist is also required so that a pattern of 100 nm or less can be formed with accuracy.

As a conventionally popular resist, diazonaphthoquinone-novolak type resists based on a dissolution inhibition effect of a diazonaphthoquinone compound on a phenolic resin material have been known (U.S. Pat. No. 4,859,563).

When a low-molecular weight phenolic resin material is used in the diazonaphthoquinone-novolak type resists, the dissolution inhibition effect of the diazonaphthoquinone compound is not sufficiently achieved, so that a development contrast between an exposed portion and an unexposed portion is low.

Lately, as a resist capable of providing a higher resolution than the diazonaphthoquinone-novolak type resist, a chemically amplified resist has been used. The chemically amplified resist generates an acid ($H^+$) by active ray irradiation and causes a deprotection reaction of an alkali-soluble group protected with an acid-degradable group, thus being solubilized in an alkali (Journal of Photopolymer Science and Technology, 17, 435 (2004)).

When a resist pattern of the chemically amplified resist is prepared, heat treatment is performed before development in order to accelerate the deprotection reaction in the presence of the acid, as a catalyst, generated at the exposed portion.

During the heat treatment, the acid is diffused by heat in a length of approximately 10 nm ("Proc. SPIE", 6154, 710 (2006)). As a result, line edge roughness (LER), which is minute projections and recesses at an edge portion of the resist pattern, is generated and the acid diffusion leads to a decrease in resolution.

Another factor causing the LER may includes an influence of a molecular weight of a base compound. Herein, the base compound means a compound having an alkali-soluble group or a protected alkali-soluble group in a resist composition.

Dissolution of the base compound in a developing liquid is caused at one molecule unit of the base compound, so that the LER is larger with a large molecular weight.

A lower molecular weight compound has a lower glass transition temperature and a lower melting point. The chemically amplified resist has a long acid diffusion length when the heat treatment before development is performed at a temperature higher than a glass transition temperature thereof, so that a resultant resolution is decreased.

In other words, the base compound for the chemically amplified resist is required to have a glass transition temperature higher than a deprotection reaction temperature in the presence of the acid catalyst. This requirement constitutes a constraint on a lower LER design, i.e., a lower molecular weight design of the chemically amplified resist.

DISCLOSURE OF THE INVENTION

A principal object of the present invention is to provide a photosensitive compound capable of forming a resist pattern with a low LER (line edge roughness).

Another object of the present invention is to provide a photosensitive composition in which the photosensitive compound is dissolved in a solvent, a resist pattern forming method using the photosensitive composition, and a device production process using the resist pattern forming method.

According to a first aspect of the present invention, there is provided a photosensitive compound comprising:

two or more structural units, in a molecule, represented by the following general formula (1):

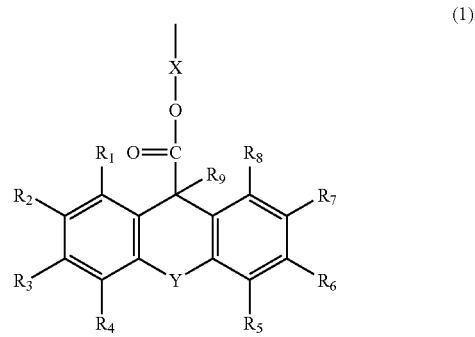

(1)

wherein $R_1$ to $R_8$ are selected from the group consisting of a hydrogen atom, a halogen atom, an alkyl group, an alkoxy group, an acetoxy group, a phenyl group, a naphthyl group, and an alkyl group in which some or all of the hydrogen atoms are optionally replaced by fluorine atoms; $R_9$ is a hydrogen atom or a hydroxyl group; X is a substituted or unsubstituted phenylene group or a substituted or unsubstituted naphthalene group; and Y is an oxygen atom or a single bond.

According to a second aspect of the present invention, there is provided a photosensitive compound comprising:

two or more structural units, in a molecule, represented by the following general formula (2):

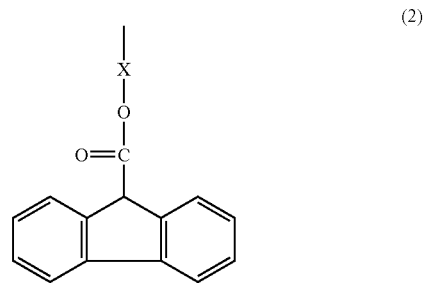

(2)

wherein X is a substituted or unsubstituted phenyl group or a substituted or unsubstituted naphthalene group.

According to a third aspect of the present invention, there is provided a photosensitive compound comprising:

two or more structural units, in a molecule, represented by the following general formula (3):

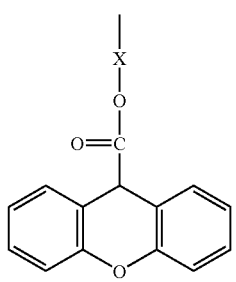

(3)

wherein X is a substituted or unsubstituted phenyl group or a substituted or unsubstituted naphthalene group.

According to a fourth aspect of the present invention, there is provided, as a photosensitive compound, a polyhydroxystyrene comprising:

hydrogen atoms of two or more phenolic hydroxyl groups substituted with a chemical group represented by the following general formula (4):

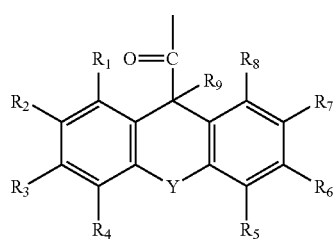

(4)

wherein $R_1$ to $R_8$ are selected from the group consisting of a hydrogen atom, a halogen atom, an alkyl group, an alkoxy group, an acetoxy group, a phenyl group, a naphthyl group, and an alkyl group in which some or all of the hydrogen atoms are optionally replaced by fluorine atoms; $R_9$ is a hydrogen atom or a hydroxyl group; and Y is an oxygen atom or a single bond.

According to a fifth aspect of the present invention, there is provided, as a photosensitive compound, a calixarene comprising:

hydrogen atoms of two or more phenolic hydroxyl groups substituted with a chemical group represented by the following general formula (4):

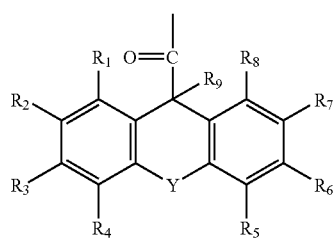

(4)

wherein $R_1$ to $R_8$ are selected from the group consisting of a hydrogen atom, a halogen atom, an alkyl group, an alkoxy group, an acetoxy group, a phenyl group, a naphthyl group, and an alkyl group in which some or all of the hydrogen atoms are optionally replaced by fluorine atoms; $R_9$ is a hydrogen atom or a hydroxyl group; and Y is an oxygen atom or a single bond.

According to a sixth aspect of the present invention, there is provided, as a photosensitive compound, a novolak resin comprising:

hydrogen atoms of two or more phenolic hydroxyl groups substituted with a chemical group represented by the following general formula (4):

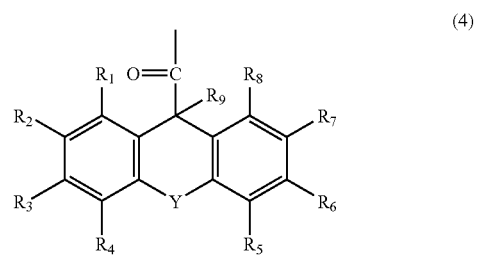

(4)

wherein $R_1$ to $R_8$ are selected from the group consisting of a hydrogen atom, a halogen atom, an alkyl group, an alkoxy group, an acetoxy group, a phenyl group, a naphthyl group, and an alkyl group in which some or all of the hydrogen atoms are optionally replaced by fluorine atoms; $R_9$ is a hydrogen atom or a hydroxyl group; and Y is an oxygen atom or a single bond.

The present invention includes a photosensitive composition, a resist pattern forming method, and a device production method.

The photosensitive composition of the present invention is characterized in that at least one species of the photosensitive compound of the present invention is dissolved in an organic solvent.

The resist pattern forming method of the present invention is characterized by comprising a step of forming a photosensitive resist layer by applying a photosensitive composition onto a substrate; a step of selectively irradiating the resist layer; and a step of forming a pattern of the resist layer by developing an irradiated portion of the resist layer.

The device production process of the present invention is characterized in that a device is formed on a substrate by using the resist pattern forming method of the present invention.

According to the present invention, it is possible to provide a photosensitive compound capable of forming a resist pattern with a low LER, a photosensitive composition in which the photosensitive compound is dissolved in an organic solvent, a resist pattern forming method using the photosensitive composition, and a device production process using the resist pattern forming method.

These and other objects, features and advantages of the present invention will become more apparent upon a consideration of the following description of the preferred embodiments of the present invention taken in conjunction with the accompanying drawings.

BEST MODE FOR CARRYING OUT THE INVENTION

Figure 1:
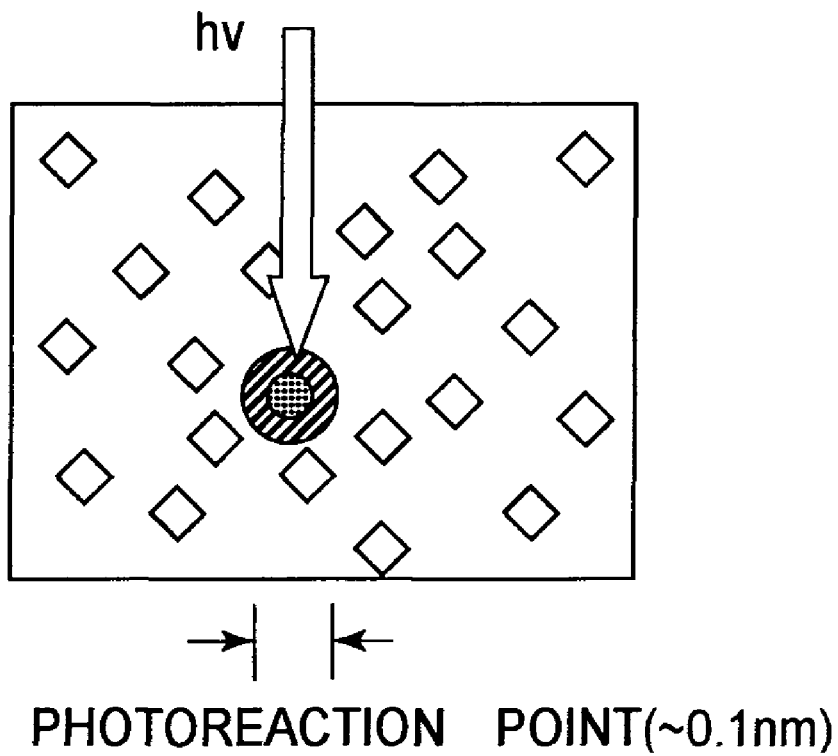
FIG. 1 is a schematic view for illustrating a photochemical reaction of a photosensitive composition according to the present invention.

In the present invention, the LER is defined as $3\sigma$, wherein $\sigma$ represents a standard deviation of a line pattern width.

The thus defined LER is calculated from measured values of line pattern widths as a population. More specifically, in a line pattern including lines with lengths from 0.5 µm to 2 µm, sampling is made at 50 points or more at regular intervals of 10 nm with respect to a line length direction and a line pattern width is measured at each of the points. The LER is calculated from the measured values of the line pattern widths. For the measurement of the line pattern widths, it is possible to use a scanning electron microscope, an atomic force microscope, or the like.

Hereinbelow, the present invention will be described more specifically.

The photosensitive compound according the first aspect of the present invention, comprises two or more structural units, in a molecule, represented by the following general formula (1):

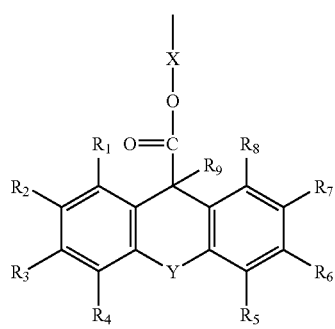

wherein $R_1$ to $R_8$ are selected from the group consisting of a hydrogen atom, a halogen atom, an alkyl group, an alkoxy group, an acetoxy group, a phenyl group, a naphthyl group, and an alkyl group in which some or all of the hydrogen atoms are optionally replaced by fluorine atoms; $R_9$ is a hydrogen atom or a hydroxyl group; X is a substituted or unsubstituted phenylene group or a substituted or unsubstituted naphthalene group; and Y is an oxygen atom or a single bond.

The photosensitive compound according to the second aspect of the present invention comprises two or more structural units, in a molecule, represented by the following general formula (2):

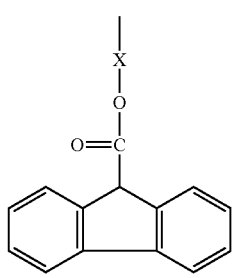

wherein X is a substituted or unsubstituted phenyl group or a substituted or unsubstituted naphthalene group.

The photosensitive compound according to the third aspect of the present invention comprises two or more structural units, in a molecule, represented by the following general formula (3):

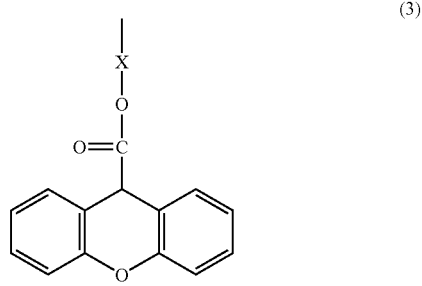

wherein X is a substituted or unsubstituted phenyl group or a substituted or unsubstituted naphthalene group.

The polyhydroxystyrene as the photosensitive compound according to the fourth aspect of the present invention comprises hydrogen atoms of two or more phenolic hydroxyl groups substituted with a chemical group represented by the following general formula (4):

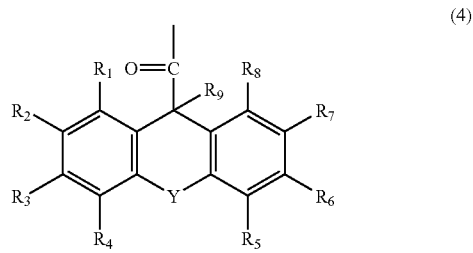

wherein $R_1$ to $R_8$ are selected from the group consisting of a hydrogen atom, a halogen atom, an alkyl group, an alkoxy group, an acetoxy group, a phenyl group, a naphthyl group, and an alkyl group in which some or all of the hydrogen atoms are optionally replaced by fluorine atoms; $R_9$ is a hydrogen atom or a hydroxyl group; and Y is an oxygen atom or a single bond.

The calixarene as the photosensitive compound according to the fifth aspect of the present invention comprises hydrogen atoms of two or more phenolic hydroxyl groups substituted with a chemical group represented by the following general formula (4):

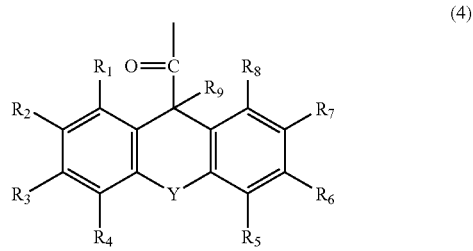

wherein $R_1$ to $R_8$ are selected from the group consisting of a hydrogen atom, a halogen atom, an alkyl group, an alkoxy group, an acetoxy group, an phenyl group, a naphthyl group, and an alkyl group in which some or all of the hydrogen atoms are optionally replaced by fluorine atoms; $R_9$ is a hydrogen atom or a hydroxyl group; and Y is an oxygen atom or a single bond.

The novolak resin as the photosensitive compound according to the sixth aspect of the present invention comprises hydrogen atoms of two or more phenolic hydroxyl groups substituted with a chemical group represented by the following general formula (4):

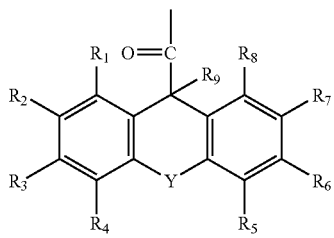

(4)

wherein $R_1$ to $R_8$ are selected from the group consisting of a hydrogen atom, a halogen atom, an alkyl group, an alkoxy group, an acetoxy group, a phenyl group, a naphthyl group, and an alkyl group in which some or all of the hydrogen atoms are optionally replaced by fluorine atoms; $R_9$ is a hydrogen atom or a hydroxyl group; and Y is an oxygen atom or a single bond.

The photosensitive compound comprising two or more structural units, in a molecule, represented by the above-described general formula (1) can be synthesized by the following method.

This photosensitive compound can be synthesized through a condensation reaction between a fluorenecarboxylic acid derivative or a xanthenecarboxylic acid derivative represented by a general formula (21) shown below with a polyhydric phenolic compound having two or more phenolic hydroxyl groups in a molecule (hereinafter referred to as a "polyphenolic compound"). By this condensation reaction, a phenolic hydroxyl group is fluorene-carboxylated or xanthene-carboxylated to provide the structural units represented by the above-described general formula (1).

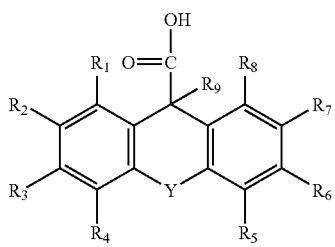

(21)

In the general formula (21), $R_1$ to $R_9$ and Y are as defined above.

Examples of the fluorenecarboxylic acid derivative or xanthenecarboxylic acid derivative represented by the general formula (21) may include fluorenecarboxylic acid, 9-hydroxyfluorenecarboxylic acid, chlorofluorenol, and xanthenecarboxylic acid.

In the present invention, the polyphenolic compound can be classified as a polymeric compound and a low molecular weight compound. In the present invention, it is preferable that a polymeric compound having a molecular weight dispersion of 1.0 or more and 1.5 or less or a low molecular weight compound having a molecular weight dispersion of 1.0 or more and 1.5 or less be used. In the present invention, the low molecular weight compound means a compound having a molecular weight of 2000 or less or a compound that is not a polymer obtained from one or more species of monomers.

The photosensitive compound of the present invention does not require heating after light exposure. For this reason, even a low molecular weight compound, which cannot be used for the chemically amplified resist due to the limitation on the glass transition temperature and the melting point, can be used in the present invention, so that a resist pattern with a low LER is formed by using the photosensitive compound of the present invention.

Examples of the polymeric polyphenolic compound in the present invention may include condensation reaction products between phenols and aldehydes, condensation reaction products between phenols and ketones, vinylphenol polymers, such as polyhydroxystyrene, and isopropenylphenol polymers.

The polymeric polyphenolic may have a weight-average molecular weight of 1,000 or more and 100,000 or less, preferably 3,000 or more and 50,000 or less and a molecular weight dispersion of 1.0 or more and 3.0 or less, preferably 1.0 or more and 1.2 or less.

Particularly, a polyhydroxystyrene homopolymer having a weight-average molecular weight of 3,000 or more and 50,000 or less and a molecular weight dispersion of 1.0 or more and 1.2 or less is preferred. This is because a lower molecular weight dispersion provides a smaller LER.

Examples of the condensation reaction products between the phenols and the aldehydes may include a phenol-novolak resin, a cresol-novolak resin, a calixarene, and the like.

Examples of the phenols used in the synthesis of the condensation reaction product between the phenols and the aldehydes may include monohydric phenols, such as phenol, cresol, xylenol, ethylphenol, propylphenol, butylphenol, and phenylphenol, and polyhydric phenols, such as resokinol, pyrocatecol, hydroquinone, bisphenol A, and pyrogallol.

Examples of the aldehydes may include formaldehyde, acetaldehyde, benzaldehyde, and terephthalaldehyde.

Examples of the ketones may include acetone, methyl ethyl ketone, diethyl ketone, and diphenyl ketone.

These condensation reactions can be performed according to an ordinary method.

The vinylphenol polymer is selected from a homopolymer of vinylphenol (hydroxystyrene) and copolymers thereof with a copolymerizable component. Examples of the copolymerizable component may include acrylic acid, methacrylic acid, styrene, maleic anhydride, maleimide, vinyl acetate, acrylonitrile, and derivatives thereof.

The isopropenylphenol polymer is selected from a homopolymer of isopropenylphenol and copolymers thereof with a copolymerizable component.

Examples of the copolymerizable component may include acrylic acid, methacrylic acid, styrene, maleic anhydride, maleimide, vinyl acetate, acrylonitrile, and derivatives thereof.

Examples of the low-molecular weight polyphenolic compound may include calixarene derivatives and compounds represented by the following general formulas (31) to (36):

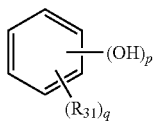
(31)

wherein $R_{31}$ is an alkyl group having 1-4 carbon atoms, a phenyl group, or a 1-naphthyl group; each $R_{31}$ may be the same or different; p is an integer of 1 or more; and q is an integer of 0 or more with the proviso that $p+q \leqq 6$.

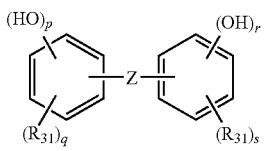
(32)

wherein $R_{31}$ is the same as in the general formula (31); Z is a single bond, —S—, —O—, —CO—, —COO—, —SO—, —C($R_{32}$)$_2$— (where $R_{32}$ is a hydrogen atom, an alkyl group having 1-6 carbon atoms, an acryl group having 2-11 carbon atoms, a phenyl group, or a naphthyl group, and each $R_{32}$ may be the same or different), or a group represented by the following general formula (33):

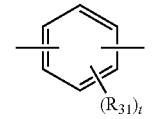
(33)

wherein $R_{31}$ is the same as in the general formula (31), and t is an integer of 0-4; and p, q, r and s are, respectively, integers of 0 or more satisfying $p+q \leqq 5$, $r+s \leqq 5$, and $p+r \geqq 1$.

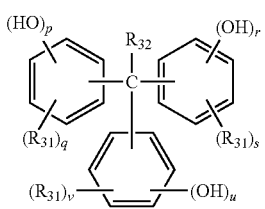
(34)

wherein $R_{31}$ is the same as in the general formula (31); $R_{32}$ is the same as in the general formula (32); and p, q, r, s, u and v are, respectively, integers of 0 or more satisfying $p+q \leqq 5$, $r+s \leqq 5$, $u+v \leqq 5$, and $p+r+u \geqq 1$.

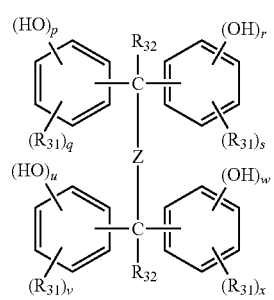
(35)

wherein $R_{31}$ is the same as in the general formula (31); $R_{32}$ and Z are the same as in the general formula (32); each $R_{31}$ may be the same or different; each $R_{32}$ may be the same or different; and p, q, r, s, u, v, w and x are, respectively, integers of 0 or more satisfying $p+q \leqq 5$, $r+s \leqq 5$, $u+v \leqq 5$, $w+x \leqq 5$, and $p+r+u+w \geqq 1$.

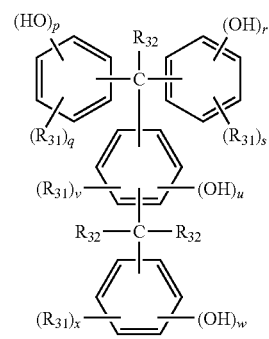
(36)

wherein $R_{31}$ is the same as in the general formula (31); $R_{32}$ is the same as in the general formula (32); each $R_{31}$ may be the same or different; each $R_{32}$ may be the same or different; and p, q, r, s, u, v, w and x are, respectively, integers of 0 or more satisfying $p+q \leqq 5$, $r+s \leqq 5$, $u+v \leqq 5$, $x+w \leqq 5$, and $p+r+u+w \geqq 1$.

In the above-described polycondensation reactions, all phenolic hydroxyl groups are not necessarily required to be fluorene-carboxylated or xanthene-carboxylated. It is preferable that, in a molecule, there are two or more fluorene- or xanthene-carboxylated phenolic groups and a degree of fluorene- or xanthene-carboxylation is 10% or more and 90% or less, particularly 10% or more and 50% or less.

When the degree of the fluorene- or xanthene-carboxylation is excessively high, resist pattern formation requires a large amount of light exposure and adhesiveness of the resist with respect to a substrate to be processed is low due to a low polarity. When the degree of the fluorene- or xanthene-carboxylation is less than 10%, the resist pattern has a low resistance to a developing liquid.

The photosensitive compound of the present invention, e.g., as described in J. Chem. Soc., 3571 (1965), directly generates a phenolic hydroxyl group as an alkali-soluble group through a photochemical reaction represented by a reaction formula shown below. In other words, the photosensitive compound functions as a positive resist dissolved in an alkaline developing liquid at an exposed portion.

PHTOCHEMICAL REACTION OF PHENYLFLUORENE CAROXYLATE

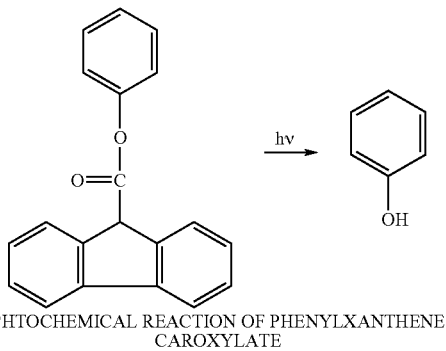

PHTOCHEMICAL REACTION OF PHENYLXANTHENE CAROXYLATE

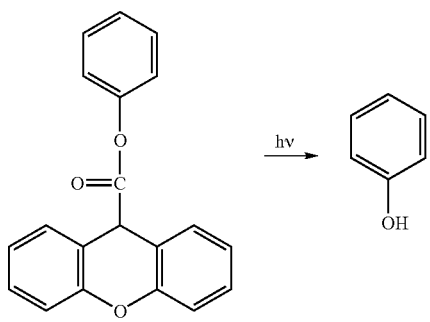

EXAMPLE

During use, the photosensitive compound of the present invention is prepared as a photosensitive composition by being dissolved in a solvent, e.g., with a solid content (concentration) of 0.1 wt. % or more and 50 wt. % or less. The photosensitive composition may desirably be filtered through a filter with a pore diameter of about 0.1-0.2 μm.

The solvent may be basically any solvent and can be selected freely depending on the purpose, so long as the solvent dissolves the photosensitive compound of the present invention and does not react with the photosensitive composition.

Examples of the solvent may include ethers, esters, ether esters, ketones, ketone esters, amides, amide esters, lactams, lactones, and (halogenated) hydrocarbons. More specifically, the solvent may include ethylene glycol monoalkyl ethers, diethylene glycol dialkyl ethers, ethylene glycol monoalkyl ether acetates, propylene glycol monoalkyl ether acetates, propylene glycol monoalkyl ethers, propylene glycol dialkyl ethers, acetate esters, hydroxyacetate esters, lactate esters, alkoxyacetate esters, cyclic or acyclic ketones, acetoacetate esters, pyruvate esters, propionate esters, N,N-dialkylformamides, N,N-dialkylacetamides, N-alkylpyrrolidones, γ-lactones, (halogenated) aliphatic hydrocarbons, and (halogenated) aromatic hydrocarbons.

Specific examples of the solvents may include ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, ethylene glycol mono-n-propyl ether acetate, propylene glycol monomethyl ether acetate (PGMEA), propylene glycol monoethyl ether acetate, propylene glycol mono-n-propyl ether acetate, isopropenyl acetate, isopropenyl propionate, toluene, xylene, methyl ethyl ketone, cyclohexanone, 2-heptanone, 3-heptanone, 4-heptanone, ethyl 2-hydroxypropionate, ethyl 2-hydroxy-2-methylpropionate, ethyl ethoxyacetate, ethyl hydroxyacetate, methyl 2-hydroxy-3-methylbutyrate, 3-methoxybutyl acetate, 3-methyl-3-methoxybutyl acetate, 3-methyl-3-methoxybutyl propionate, 3-methyl-3-methoxybutyl butyrate, ethyl acetate, n-propyl acetate, n-butyl acetate, methyl acetoacetate, ethyl acetoacetate, methyl 3-methoxypropionate, ethyl 3-methoxypropionate, methyl 3-ethoxypropionate, ethyl 3-ethoxypropionate, N-methylpyrrolidone, N,N-dimethylformamide, and N,N-dimethylacetamide.

Of these solvents, in view of ease of handling, propylene glycol monomethyl ether acetate (PGMEA), ethyl-2-hydroxypropionate, cyclohexanone, and the like may desirably be used. These solvents may be used singly or as a mixture of two or more solvents.

The above-mentioned solvent may contain one or more high-boiling solvents as desired. Examples of the high-boiling solvent may include benzyl ethyl ether, di-n-benzyl ether, diethylene glycol monomethyl ether, diethylene glycol monoethyl ether, acetonylacetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, and ethylene glycol monophenyl ether acetate.

The photosensitive composition of the present invention may contain a surfactant.

Examples of the surfactant may include fluorine-containing surfactants; silicone-containing surfactants; polyoxyethylene alkyl ethers, such as polyoxyethylene lauryl ether, polyoxyethylene stearyl ether, and polyoxyethylene oleyl ether; polyoxyethylene aryl ethers, such as polyoxyethylene octyl phenyl ether, and polyoxyethylene nonyl phenyl ether; and polyoxyethylene dialkyl esters, such as polyoxyethylene dilaurate, and polyoxyethylene distearate. By adding the surfactant, it is possible to control the adhesiveness with respect to the substrate and wettability with respect to the developing liquid.

Commercially available surfactants may include BM-1000, and BM-1100 (BM Chemie Co.); Megafack F142D, F144D, F171, F172, F173, F177, F178A, F178K, F179, F183, F184, and F191 (Dainippon Ink & Chemicals Inc.); Florard FC-135, FC-170C, FC-171, FC-176, FC-430, and FC-431; Megafack RS-1, RS-7, RS-9, RS-15, and R-08 (Sumitomo 3M Ltd.); Surflon S-112, S-113, S-131, S-141, S-145, S-382, SC-101, SC-102, SC-103, SC-104, SC-105, and SC-106 (Asahi Glass Co.); F-Top EF301, EF303, and EF 352 (Shin Akita Kasei K.K.); SH-28PA, SH-190, SH-193, SZ-6032, SF-8428, DC-57, and DC-190 (Dow Corning Toray Silicone Co., Ltd.); Organosiloxane Polymer KP341 (Shin-Etsu Chemical Co., Ltd.); (meth)acrylate type copolymers Polyflow No. 57, No. 95 (Kyoeisha Kagaku K.K.); Ftargent FT-250, FT-251, and FTX-218 (Neos Co., Ltd.); etc.

These surfactants may be ordinarily used in an amount of 0.2 wt. part or less per the total amount (100 wt. parts) of the photosensitive compound, preferably in an amount of 0.001 wt. part or more and 0.05 wt. part or less, more preferably in an amount of 0.003 wt. part or more and 0.02 wt. part or less.

The photosensitive composition may further contain known additives, such as a colorant, an adhesive aid, a storage stabilizer, a defoaming agent, and the like, as desired.

A solution of the photosensitive composition of the present invention can be applied by a known application apparatus, such as a spin coater, a dip coater, and a roller coater by a known method. A thickness of the applied film (layer) may be freely set depending on the use of the film, but the solution may desirably be applied to provide a film (layer) thickness of 0.01 μm or more and 5 μm or less after prebaking.

In the case where a minute pattern is formed by using near-field light, it is desirable that the film (layer) thickness may generally be 30 nm or less, preferably be 20 nm or less (e.g., 10-20 nm).

A material for the substrate onto which the photosensitive composition is applied may include metals, semiconductors, glass, quartz, BN, and organic materials. The substrate may be coated with a single film of or a plurality of films of a resist, a spin-on-glass material, an organic substance, a metal, an oxide, a nitride, or the like.

Examples of the substrate coated with plural kinds of coating films may preferably include a substrate, which is coated with an underlying layer of a resist removable by oxygen dry-etching and a layer resistant to oxygen plasma etching formed in this order.

A resist for the underlying layer may include thermosetting phenol resin materials, but the resist is not limited thereto.

The oxygen-plasma-etching-resistant layer may be formed from $SiO_2$, $TiO_2$, or a spin-on-glass material, but is not limited thereto.

The underlying layer of the removable resist may preferably be formed with a thickness of 0.01 μm or more and 1 μm or less, and the oxygen-plasma-etching-resistant layer preferably be formed with a thickness of 0.001 μm or more and 1 μm or less.

The photosensitive resist layer is formed on the oxygen-plasma-etching-resistant layer.

The applied film of the photosensitive composition may be appropriately prepared depending on the boiling point of the solvent or the like of the photosensitive composition, but may be prebaked at a temperature of 50° C. or more and 150° C. or less, preferably 80° C. or more and 110° C. or less. The prebaking can be performed by a heating means, such as a hot-plate, a hot-air drier, or a like.

The thus applied photosensitive composition layer is ordinarily exposed to radiation imagewise and selectively through a mask by using a known exposure device. The radiation for the exposure may include visible rays, ultraviolet rays, far ultraviolet rays, X-rays, electron rays, γ-rays, molecular beams, and ion beams. These types of radiation may be selected and used appropriately. In a preferred embodiment, mercury lamp beams (wavelengths: 436 nm, 365 nm, 254 nm), a KrF excimer laser beam (wavelength: 248 nm), an ArF excimer laser beam (wavelength: 193 nm), an $F_2$ excimer laser beam (wavelength: 157 nm), far ultraviolet beams, such as an extreme ultraviolet beam (EUV, wavelength: 13 nm), and electron beams are used. These types of radiation may be employed singly or as a combination of two or more types.

As another exposure method, it is possible to preferably employ a method in which near-field light is generated by a photomask including a light-blocking layer having an opening width smaller than the wavelength of the exposure light source. As the radiation for the near-field light exposure, the above-mentioned types of radiation can be used. These types may be used singly or in combination of two or more types. The near-field light exposure is conducted by bringing the light-blocking layer and an object to be exposed close to each other (e.g. into close contact with each other) so that the near-field light passing through an opening in the light-blocking layer constituting the mask can reach the object to be exposed.

In order to obtain a finer resist pattern, it is particularly preferable that the exposure be performed with shorter wavelength beams, such as ArF excimer laser beams, $F_2$ excimer laser beams, EUV beams, electron beams, and near-field light, which is not affected by a diffraction limit.

Next, the photochemical reaction of the photosensitive composition of the present invention will be described.

Figure 2:
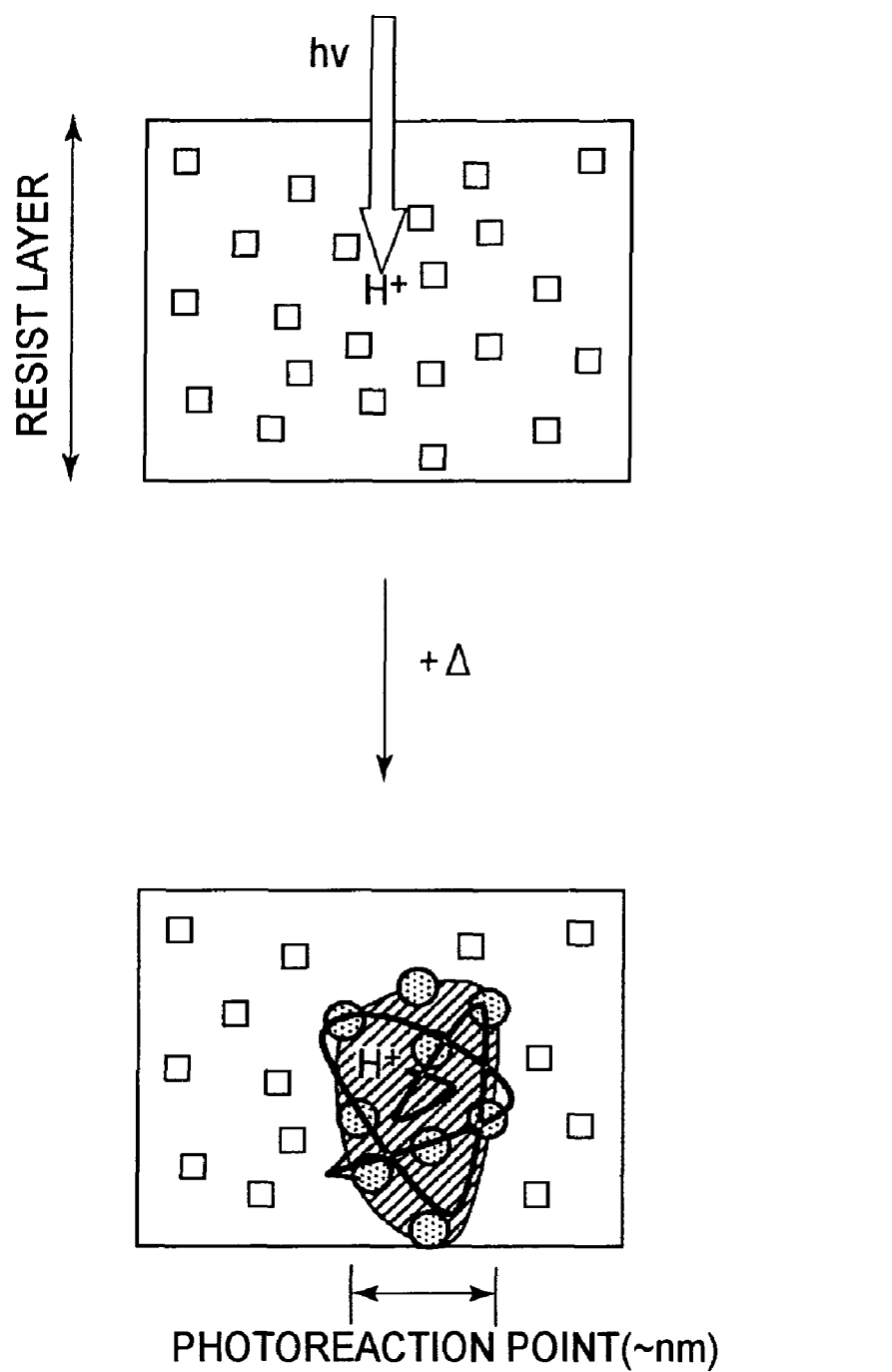
FIG. 2 is a schematic view for illustrating a photochemical reaction of a conventional chemically amplified resist.

FIG. 1 is a schematic view for illustrating a photochemical reaction of the photosensitive composition of the present invention and FIG. 2 is a schematic view for illustrating a photochemical reaction of a conventional chemically amplified resist.

In the resist shown in FIG. 2, one photon generates one acid functioning as a catalyst and the acid induces a plurality of deprotection reactions while diffusing by heating before development to produce a plurality of alkali-soluble groups. In the present invention, the heating before the development performed in the conventional chemically amplified resist is not required. Here, a photoreaction point (spot) referred to in the present invention is defined as a region in which one photon is capable of inducing the deprotection reaction, as shown in FIG. 1.

In the chemically amplified resist, one photon generates one acid functioning as a catalyst and the acid induces a plurality of deprotection reactions while diffusing by heat, whereas in the photosensitive compound of the present invention, one photon induces one deprotection reaction.

Therefore, one photoreaction point in the chemically amplified resist has a size of about 10 nm. The photoreaction point of the photosensitive compound of the present invention has a size on a molecular scale (0.1 nm or more and 1 nm or less), so that a resist pattern can be formed with a small LER.

After the exposure, the exposed portion (irradiated portion) of the photosensitive composition is developed and removed to obtain an intended resist pattern.

Examples of the developing liquid used for the development may include aqueous alkaline solutions containing compounds dissolved therein, such as sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, choline, 1,8-diazabicyclo[5.4.0]-7-undecene, and 1,5-diazabicyclo[4.3.0]-5-nonene. It is also possible to add to these aqueous alkaline solutions an appropriate amount of a water-soluble organic solvent, such as methanol and ethanol, or a surfactant. An aqueous 2.38 wt. %-tetramethylammonium hydroxide solution is particularly preferred.

The development may be conducted by dipping, spraying, brushing, slapping, or a like method. Thereafter, the resist is washed and dried to obtain a desired resist pattern.

In the case where the resist pattern is formed in a film on a substrate having an underlying layer of a resist removable by oxygen dry-etching and an oxygen-plasma-etching-resistant layer formed thereon in this order, first, the oxygen plasma-etching-resistant layer is etched through the above-mentioned resist pattern as the mask. Wet etching and dry etching may be used, but dry etching is suitable for fine pattern formation and is preferred. An alkaline for the wet etching is selected depending on an object to be etched, and examples thereof may include hydrofluoric acid solutions, aqueous ammonium fluoride solutions, aqueous phosphoric acid solutions, aqueous acetic acid solutions, aqueous nitric acid solutions, and aqueous cerium ammonium nitrate solutions.

The gas for the dry etching may include CHF$_3$, CF$_4$, C$_2$F$_6$, SF$_6$, CCl$_4$, BCl$_3$, Cl$_2$, HCl, H$_2$, and Ar, and the like gas. These gases may be used in a mixture, as desired.

Next, oxygen plasma etching is conducted through the pattern of the oxygen-plasma-etching-resistant layer, as the mask, onto which the resist pattern is transferred. The oxygen-containing gas for the oxygen plasma etching may include, e.g., oxygen alone, mixtures of oxygen with an inert gas, such as argon, mixtures of oxygen with carbon monoxide, carbon dioxide, ammonia, dinitrogen monoxide, or sulfur dioxide.

Through the above two-step etching, a resist pattern can be formed with a higher aspect ratio than a resist pattern after the exposure and the development.

With the resist pattern formed as described above as the mask, a substrate (e.g., a semiconductor substrate of silicon, germanium, or the like) is processed by dry etching, wet etching, metal vapor deposition, lift-off, plating, and the like. As a result, it is possible to produce a desired device on the substrate. More specifically, a semiconductor device can be prepared in the following manner.

First, a device circuit of a semiconductor is designed, and a mask on which a circuit pattern is formed based on the design is prepared. Separately, a substrate for the device (e.g., a silicon wafer) is prepared, and the photosensitive composition of the present invention is laminated on the substrate.

Then, the circuit is formed on the substrate through lithography by using the mask and a conventional exposure device. For the formation of the circuit, steps of oxide film formation, etching, insulation film formation, conductive wiring film formation, and patterning are performed. Next, the substrate on which the circuit is formed is subjected to an assembly process (dicing, and bonding), packaging, and the like, and is then chipped.

INDUSTRIAL APPLICABILITY

The present invention is applicable to a resist pattern forming method using a photosensitive composition capable of providing a resist pattern with a low LER and a method of processing a substrate using the resist pattern forming method.

While the invention has been described with reference to the structures disclosed herein, it is not limited to the details set forth above and this application is intended to cover such modifications or changes as may fall within the purpose of the improvements or the scope of the following claims.

The invention claimed is:

1. A calixarene comprising hydrogen atoms of two or more phenolic hydroxyl groups substituted with a chemical group represented by general formula (4):

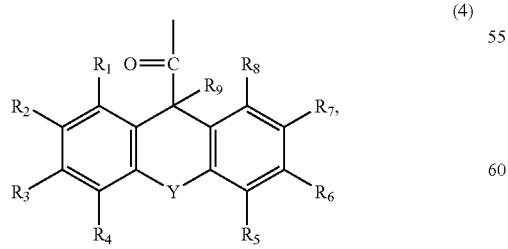

(4)

wherein R$_1$ to R$_8$ are selected from the group consisting of a hydrogen atom, a halogen atom, an alkyl group, an alkoxy group, an acetoxy group, a phenyl group, a naphthyl group, and an alkyl group in which some or all hydrogen atoms are optionally replaced with a fluorine atom; R$_9$ is hydrogen or a hydroxyl group; and Y is an oxygen atom or a single bond.

2. A resist pattern forming method comprising:

a step of forming a photosensitive resist layer by applying onto a substrate a photosensitive composition comprising:

at least one species of a photosensitive compound selected from the group consisting of compounds (i)-(iv):

(i) a compound comprising two or more structural units, in a molecule, represented by general formula (1):

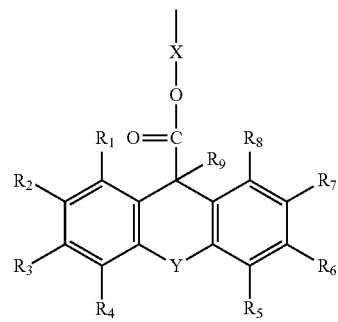

(1)

wherein R$_1$ to R$_8$ are selected from the group consisting of a hydrogen atom, a halogen atom, an alkyl group, an alkoxy group, an acetoxy group, a phenyl group, a naphthyl group, and an alkyl group in which some or all hydrogen atoms are optionally replaced with a fluorine atom; R$_9$ is hydrogen and or a hydroxyl group; X is a substituted or unsubstituted phenylene group or a substituted or unsubstituted naphthalene group; and Y is an oxygen atom or a single bond:

(ii) a compound comprising two or more structural units, in a molecule, represented by general formula (2):

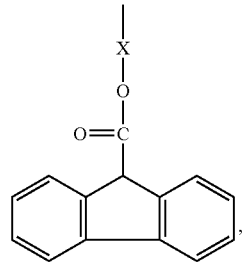

(2)

wherein X is a substituted or unsubstituted phenyl group or a substituted or unsubstituted naphthalene group;

(iii) a compound comprising two or more structural units, in a molecule, represented by general formula (3):

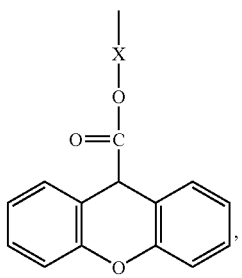

(3)

wherein X is a substituted or unsubstituted phenyl group or a substituted or unsubstituted naphthalene group; and (iv) a polyhydroxystyrene, calixarene, or novolak comprising hydrogen atoms of two or more phenolic hydroxyl groups substituted with a chemical group represented by general formula (4):

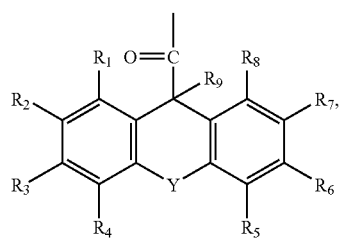

(4)

wherein $R_1$ to $R_8$ are selected from the group consisting of a hydrogen atom, a halogen atom, an alkyl group, an alkoxy group, an acetoxy group, a phenyl group, a naphthyl group, and an alkyl group in which some or all hydrogen atoms are optionally replaced with a fluorine atom; $R_9$ is hydrogen or a hydroxyl group; and Y is an oxygen atom or a single bond; and an organic solvent in which there is the at least one species of the photosensitive compound;

a step of selectively irradiating the resist layer with radiation; and a step of forming a pattern of the resist layer by developing an irradiated portion of the resist layer, wherein a resist layer removable by oxygen plasma etching and a resist layer resistant to the oxygen plasma etching are formed on the substrate in this order and thereafter on the resist layer resistant to the oxygen plasma etching, the photosensitive resist layer is formed.

3. The method according to claim 2, wherein the at least one species of the photosensitive compound is the compound (i).

4. The method according to claim 2, wherein the at least one species of the photosensitive compound is the compound (ii).

5. The method according to claim 2, wherein the at least one species of the photosensitive compound is the compound (iii).

6. The method according to claim 2, wherein the at least one species of the photosensitive compound is the compound (iv).

7. The method according to claim 6, wherein the compound (iv) is the polyhydroxystyrene.

8. The method according to claim 6, wherein the compound (iv) is the calixarene.

9. The method according to claim 6, wherein the compound (iv) is the novolak.

10. A resist pattern forming method comprising:

a step of forming a photosensitive resist layer by applying onto a substrate a photosensitive composition comprising:

at least one species of a photosensitive compound selected from the group consisting of compounds (i)-(iv):

(i) a compound comprising two or more structural units, in a molecule, represented by general formula (1):

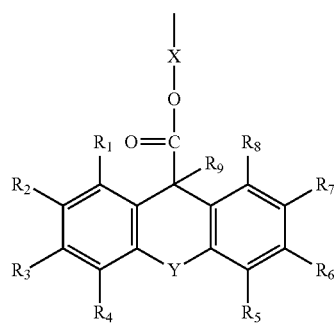

(1)

wherein $R_1$ to $R_8$ are selected from the group consisting of a hydrogen atom, a halogen atom, an alkyl group, an alkoxy group, an acetoxy group, a phenyl group, a naphthyl group, and an alkyl group in which some or all hydrogen atoms are optionally replaced with a fluorine atom; $R_9$ is hydrogen and or a hydroxyl group; X is a substituted or unsubstituted phenylene group or a substituted or unsubstituted naphthalene group; and Y is an oxygen atom or a single bond:

(ii) a compound comprising two or more structural units, in a molecule, represented by general formula (2):

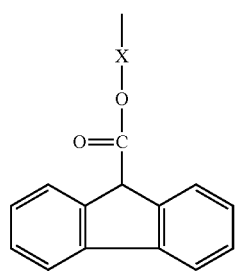

(2)

wherein X is a substituted or unsubstituted phenyl group or a substituted or unsubstituted naphthalene group;

(iii) a compound comprising two or more structural units, in a molecule, represented by general formula (3):

(3)

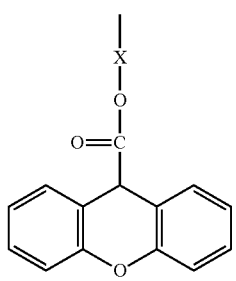

wherein X is a substituted or unsubstituted phenyl group or a substituted or unsubstituted naphthalene group; and (iv) a polyhydroxystyrene, calixarene, or novolak comprising hydrogen atoms of two or more phenolic hydroxyl groups substituted with a chemical group represented by general formula (4):

(4)

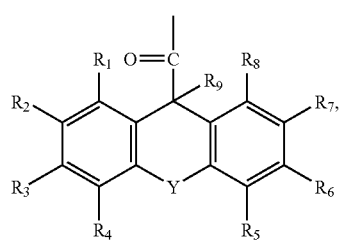

wherein $R_1$ to $R_8$ are selected from the group consisting of a hydrogen atom, a halogen atom, an alkyl group, an alkoxy group, an acetoxy group, a phenyl group, a naphthyl group, and an alkyl group in which some or all hydrogen atoms are optionally replaced with a fluorine atom; $R_9$ is hydrogen or a hydroxyl group; and Y is an oxygen atom or a single bond; and an organic solvent in which there is the at least one species of the photosensitive compound;

a step of selectively irradiating the resist layer with radiation; and a step of forming a pattern of the resist layer by developing an irradiated portion of the resist layer, wherein the photosensitive resist layer is formed in a thickness of 20 nm or less.

11. The method according to claim 10, wherein the at least one species of the photosensitive compound is the compound (i).

12. The method according to claim 10, wherein the at least one species of the photosensitive compound is the compound (ii).

13. The method according to claim 10, wherein the at least one species of the photosensitive compound is the compound (iii).

14. The method according to claim 10, wherein the at least one species of the photosensitive compound is the compound (iv).

15. The method according to claim 14, wherein the compound (iv) is the polyhydroxystyrene.

16. The method according to claim 14, wherein the compound (iv) is the calixarene.

17. The method according to claim 14, wherein the compound (iv) is the novolak.

* * * * *